United States Patent [19]

Nunn et al.

[11] 4,186,203
[45] Jan. 29, 1980

[54] 2-[GAMMA-(1-PIPERIDINYL)PROPYL]-1,2-BENZISOTHIAZOLE-3-ONE, ITS SALTS, AND PHARMACEUTICAL COMPOSITIONS

[75] Inventors: Barbara Nunn, Sutton; Keith H. Baggaley, Redhill, both of England

[73] Assignee: Beecham Group Limited, England

[21] Appl. No.: 917,069

[22] Filed: Jun. 19, 1978

[30] Foreign Application Priority Data

Jun. 20, 1977 [GB] United Kingdom ............... 25599/77

[51] Int. Cl.$^2$ .................. A61K 31/445; C07D 417/08
[52] U.S. Cl. ...................................... 424/267; 546/198
[58] Field of Search .................... 260/293.57; 546/198

[56] References Cited

U.S. PATENT DOCUMENTS

| | | | |
|---|---|---|---|
| 3,227,715 | 1/1966 | Bub | 260/327 C |
| 3,661,974 | 5/1972 | Grivas | 260/304 A |
| 4,113,728 | 9/1978 | Baggaley | 546/198 |

Primary Examiner—John M. Ford
Assistant Examiner—Robert T. Bond
Attorney, Agent, or Firm—Jacobs & Jacobs

[57] ABSTRACT

The compound 2-[gamma-(1-piperidinyl)propyl]-1,2-benzisothiazole-3-one or a pharmaceutically acceptable acid addition salt thereof and pharmaceutical compositions containing an effective amount of such compound or salt and a carrier, preferably compositions in orally administrable form. The compound or salt is characterized by antithrombotic activity, especially for inhibiting platelet aggregation. Procedures for preparation of the compound are described.

4 Claims, No Drawings

2-[GAMMA-(1-PIPERIDINYL)PROPYL]-1,2-BENZISOTHIAZOLE-3-ONE, ITS SALTS, AND PHARMACEUTICAL COMPOSITIONS

This invention relates to antithrombotic compounds and in particular to a benzisothiazolone which has particularly high activity.

Arterial thrombosis develops intially from the aggregation of blood platelets within the artery. This aggregate may eventually lead to the formation of fibrin and the formation of a consolidated occlusive thrombus. The most widely used therapy for thrombosis is the use of anti-coagulant agents, which influence blood clotting. However, although effective in venous thrombosis, where the thrombus is formed mainly of fibrin, anticoagulant therapy has no effect on platelet aggregation and has therefore limited effectiveness in arterial thrombosis. It is now accepted that anti-coagulant drugs have little to offer in the treatment of arterial thrombosis.

With the increasing recognition of the primary role of platelets in thrombosis, attention had turned to drugs which are capable of inhibiting the aggregation of platelets.

U.S. Pat. No. 3,227,715 discloses a class of benzisothiazolones of the formula (I):

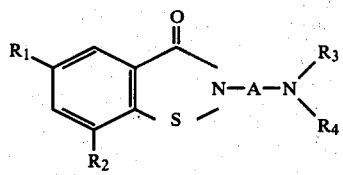

wherein A represents a lower alkylene of 2 to 4 carbon atoms, $R_1$ and $R_2$ are hydrogen or halogen, $R_3$ and $R_4$ represent hydrogen, lower alkyl, cycloalkyl, hydroxyalkyl of 2 to 4 carbon atoms or alkoxyalkyl of 2 to 4 carbon atoms, and $R_3$ and $R_4$ together with the nitrogen atom on which they are substituted stand for an unsubstituted or lower alkyl substituted heterocyclic ring having from 5 to 6 atoms in the ring; as being useful for the therapy of inflammatory processes.

U.S. Pat. No. 3,227,715 does not suggest any antithrombotic activity for any of the compounds described therein.

U.S. Pat. No. 4,113,728 claiming priority of British Patent Application No. 47373/75 discloses a related class of benzisothiazolones as being effective in inhibiting platelet aggregation.

We have now found that a benzisothiazolone compound which falls within the generic disclosure of U.S. Pat. No. 3,227,715 but is not specifically described therein or in U.S. Pat. No. 4,113,728 has exceptionally high activity in inhibiting platelet aggregation which is not predictable from the prior art.

The present invention therefore provides the compound 2-[γ-(1-piperidinyl)propyl]-1,2-benzisothiazol-3-one of formula (II), or a pharmaceutically acceptable acid addition salt thereof:

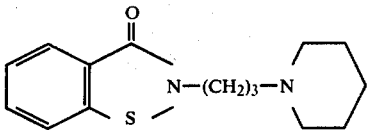

Suitable acid addition salts include inorganic salts such as sulphates, nitrate, phosphate, and borate, hydrohalides e.g. hydrochloride, hydrobromide, and hydroiodide, and organic acid addition salts such as acetate, oxalate, tartrate, maleate, citrate, succinate, benzoate, ascorbate, methanesulphonate, and p-toluenesulphonate.

Preferred salts are the hydrochloride and hydrobromide.

The compound of this invention may be prepared by reacting a compound of formula (III):

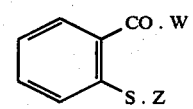

wherein W and Z are the same or different and each is a halogen atom; with a compound of formula (IV):

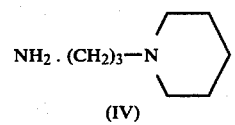

Preferably W is chlorine and Z is chlorine or bromine. Suitable solvents for the reaction include carbon tetrachloride or other halogenated hydrocarbon solvents.

A second method for the preparation of the compound of formula (II) comprises reaction of a compound of formula (V) or a salt thereof:

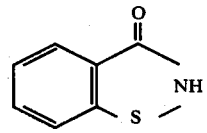

with a compound of formula (VI):

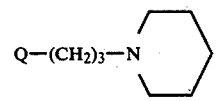

wherein Q is a readily displaceable group. Suitably, Q is a halogen atom. Preferably the compound (VI) is used as its alkali metal salt, for example the sodium salt.

In this reaction a solvent such as dimethyl formamide or dimethylsulphoxide may be used, preferably at elevated temperatures. In general the corresponding 3-ether is also formed and the desired product may be separated by crystallisation, distillation and chromatographic techniques.

Compound of formula (II) may also be prepared by treating a compound of formula (VII):

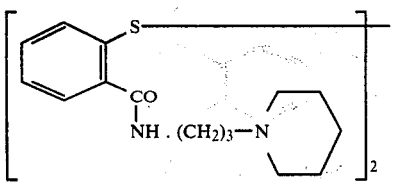

with either a base or with chlorine or bromine.

Suitable bases include 10% sodium hydroxide or other aqueous alkali and the reaction may be carried out at room temperature or elevated temperatures. If chlorine is employed in this reaction it may be bubbled into a solution of compound (VII) in an inert solvent such as carbon tetrachloride.

The compound of formula (II) may also be prepared by treating a compound a formula (VIII):

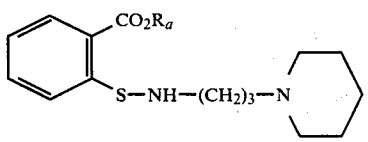

wherein $CO_2R_a$ is a carboxylic ester group; with a base.

Suitably the group $R_a$ is an alkyl or aryl group. Suitable bases for the reaction include alkali metal alkoxides, alkali metal hydroxides and tetramethylammonium hydroxide in lower alcohols.

The invention also provides a pharmaceutical composition which comprises a compound of formula (I) as defined above together with at least one pharmaceutically acceptable carrier.

As is common practice, such composition will usually be accompanied by or associated with written or printed directions for use in the medical treatment concerned, in this case as an agent for the inhibition of platelet aggregation or thrombus formation.

The composition may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl-pyrolidone; fillers, for example lactose, sugar, maize-starch, calcium phosphate, sorbitol or glycine; tabletting lubricants, for example magnesium stearate, talc, polyethylene glycol, or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, aluminium stearate gel or hydrogenated edible fats, emulsifying agents, for example lecithin, sorbitan monooleate, or acacia; nonaqueous vehicles (which may include edible oils), for example almond oil, fractionated coconut oil, oily esters such as glycerine, porpylene glycol, or ethyl alcohol; preservatives, for example methyl or propyl p-hydroxybenzoate sorbic acid, and if desired conventional flavouring or colouring agents. The compound may also if desired by incorporated in a foodstuff, for example in the form of a biscuit.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration. Where the compositions comprise dosage units, each unit will preferably contain from 1-500 mg., of the active ingredient.

The dosage employed for adult treatment will of course depend on the dose-response characteristics of the particular active ingredient, and also on the blood volume and condition of the patient, but will normally be in the range 0.01 to 30 mg/kg/day depending on the route and frequency of administration. The preferred does is 10 to 500 mg., orally 1 to 3 times a day for an adult human.

The compositions of the invention are useful for administration to humans and animals to prevent clot formation for example after surgery to prevent postoperative thrombosis; in geriatric patients to prevent transient cerebral ischemic attacks; and long-term prophylaxis following myocardial infarcts and strokes.

The compounds of formula (II) may also have applications in the storage of whole blood in blood banks, and whole blood to be used in heart-lung machines, or to be circulated through organs, e.g. heart and kidneys, which have been removed from a cadaver and prior to transplant.

The following example illustrates the invention.

Example

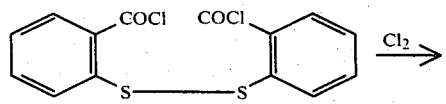

-continued

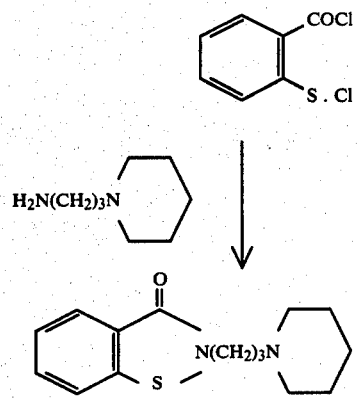

Dry chlorine was passed into a suspension of 2,2'-dithiodibenzoyl chloride (2.41 g, 7.03 m.mole) in dry CCl$_4$ (50 ml) until solution was complete. Excess of chlorine was removed by passing nitrogen through the reaction mixture, the solution was filtered, and the filtrate was added dropwise with stirring to a solution of N-(3-aminopropyl)piperidine (6.0 g, 42.25 mmole) in dry CCl$_4$ (100 ml) at room temperature.

The reaction mixture was transferred to a separating funnel with dichloromethane and the suspension was washed with 10% aqueous sodium hydroxide solution, water and brine. The organic layer was dried (anhydrous MgSO$_4$), evaporated, and the residue was chromatographed on silica gel (150 g) using dichloromethane-methanol (90:10) as eluant.

A solution of the product in diisopropyl ether was treated with animal charcoal, filtered, evaporated and the residue (c.1.3 g) was recrystallised from diisopropyl ether giving 2-γ-(piperidino) propyl-1,2-benzisothiazol-3-one as colourless needles, 720 mg, (18.5%), m.p 71.5°–73°.

Biological Data

The compound of the Example was tested for its ability to inhibit platelet aggregation in the guinea pig ex vivo by the method given below, and was compared with two closely related compounds disclosed in U.S. Pat. No. 3,227,715, and also with two compounds disclosed in British Patent Application No. 47373/75, as well as with three known anti-aggregant compounds.

Method

Ten male guinea pigs weighing 250–300 g were orally dosed 1% methyl cellulose (5 ml/kg) in which the compound under test was suspended. Ten control animals were given methyl cellulose alone. Two hours later, each animal was killed and 4.5 ml blood drawn from the inferior vena cava into 0.5 ml trisodium citrate dihydrate. Platelet-rich-plasma (PRP) was prepared from each blood sample by centrifugation at 450 g for 5 min. The platelet concentration in each sample of PRP was adjusted with autologous platelet-poor plasma to give a count of 500,000 platelets/ul P.R.P. Aggregation was measured turbidometrically (G. V. R. Born, 1962 Nature, 194, 927–929) at 37° using a Bryston aggregometer coupled to a pen-recorder. The concentration of collagen producing approximately 50% maximal aggregation and the concentration of ADP producing first-phase aggregation were compared in PRP samples from control and drug treated animals. Results are summarised in Table 1 together with some known anti-aggregant compounds for comparison.

In Table 1 the dose ratio represents the ratio of the concentration of aggregating agent to cause aggregation in PRP from drug-treated animals to the concentration of aggregating agent to cause aggregation in PRP from control animals.

Table 1 gives the results of the compound of this invention (compound A), two compounds disclosed in Application 47373/75 (compounds B and C), two compounds disclosed in U.S. Pat. No. 3,227,715 (compounds D and E) and three known anti-aggregant agents (compounds F,G,H).

Table 1

| Compound Tested | Oral Dose mmol/kg | Dose Ratio Collagen | Dose Ratio ADP |
|---|---|---|---|
| A. 2-[γ-(1-piperidinyl)propyl]-1,2-benzisothiazol-3-one | 0.15 | >27* | >27* |
| B. 2-[β-(3-azabicyclo[3.2.2]-non-3-yl)ethyl]-1,2-benzisothiazol-3-one | 0.15 | 1.7 | 1.1 |
| C. 5,6-dimethoxy-2-[β-(2'-pyridyl)ethyl]-1,2-benzisothiazol-3-one | 0.15 | 1.5 | 1.1 |
| D. 2-[β-(1-piperidyl)-ethyl]-1,2,-benzisothiazol-3-one | 0.15 | >18.2* | 8.3* |
| E. 2-[β-(1-pyrrolidinyl)-ethyl]-1,2,-benzisothiazol-3-one | 0.15 | 13.9* | 1.9 |
| F. Sulfinpyrazone | 0.3 | 2.1* | 1.2 |
| G. Aspirin | 0.15 | 2.2* | 1.3 |
| H. 4-(4-morpholinyl)-2-(1-piperazinyl)-thieno[3,2-d]pyridimine dihydrochloride. | 0.15 | 3.0* | 1.3 |

It can be seen from Table I that compound A is many times more active than any other compound in Table I as an inhibitor of platelet aggregation.

We claim:

1. The compound 2-[Gamma-(1-piperidinyl)propyl]-1,2-benzisothiazol-3-one or a pharmaceutically acceptable acid addition salt thereof.

2. The compound as claimed in claim 1 in the form of its hydrochloride salt.

3. A pharmaceutical composition having antithrombotic activity which comprises an antithrombotically effective amount of a compound according to claim 1 together with at least one pharmaceutically acceptable carrier.

4. A pharmaceutical composition according to claim 3 in orally administrable form.

* * * * *